(12) United States Patent
Nebling et al.

(10) Patent No.: US 8,900,440 B2
(45) Date of Patent: Dec. 2, 2014

(54) METHOD FOR DETECTING CHEMICAL OR BIOLOGICAL SPECIES AND ELECTRODE ARRANGEMENT THEREFOR

(75) Inventors: Eric Nebling, Pinneberg (DE); Joerg Albers, Brokdorf (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 968 days.

(21) Appl. No.: 12/995,923

(22) PCT Filed: May 29, 2009

(86) PCT No.: PCT/EP2009/056616
§ 371 (c)(1),
(2), (4) Date: Mar. 17, 2011

(87) PCT Pub. No.: WO2009/147093
PCT Pub. Date: Dec. 10, 2009

(65) Prior Publication Data
US 2011/0156722 A1 Jun. 30, 2011

(30) Foreign Application Priority Data
Jun. 6, 2008 (DE) .......................... 10 2008 027 038

(51) Int. Cl.
*G01N 27/327* (2006.01)
*G01N 27/48* (2006.01)
*G01N 27/404* (2006.01)
*G01N 33/543* (2006.01)
*C12Q 1/00* (2006.01)

(52) U.S. Cl.
CPC ............... *C12Q 1/001* (2013.01); *G01N 27/48* (2013.01); *G01N 27/404* (2013.01); *G01N 2458/30* (2013.01); *G01N 33/5438* (2013.01)
USPC ...................... 205/779; 204/403.1; 204/230.5

(58) Field of Classification Search
CPC ..... G01N 27/404; G01N 27/48; G01N 27/49; G01N 27/403; G01N 27/4166–27/4168
USPC ........ 205/775, 779, 792; 204/403.01–403.15, 204/402, 229.8, 229.9, 230.1, 230.5, 230.7
See application file for complete search history.

(56) References Cited

U.S. PATENT DOCUMENTS

| 6,881,379 B1 | 4/2005 | Bredehorst et al. |
| 2007/0111202 A1 | 5/2007 | Henkens et al. |

(Continued)

FOREIGN PATENT DOCUMENTS

| DE | 4318519 A1 | 12/1994 |
| DE | 19916867 A1 | 10/2000 |

(Continued)

OTHER PUBLICATIONS

Osamu Niwa et al., 'Small-Volume Voltammetric Detection of 4-Aminophenol with Interdigitated Array Electrodes and Its Application to Electrochemical Enzyme Immunoassay'; Anal. Chem. (1993), 65, pp. 1559-1583.

(Continued)

*Primary Examiner* — J. Christopher Ball
(74) *Attorney, Agent, or Firm* — Duane Morris LLP

(57) ABSTRACT

The present invention pertains to a process for detecting one or more chemical or biological species, which can either react in a redox reaction or directly or indirectly generate a molecule, which can react in a redox reaction, wherein current generated by said redox reaction is detected at at least one electrode, comprising the following steps: 1. Positioning a quantity of the species or molecule, which quantity varies over time, on, at or in the vicinity of the at least one electrode within a period $t_1$-$t_2$, 2. switching the at least one electrode back and forth multiple times during the period $t_1$-$t_2$ between two different potentials, such that relative to a reference electrode, it assumes potentials that are in the range of the oxidation potential of said species or of said molecule or above it or in the range of the reduction potential of said species or said molecule or under it, as a result of which said species/said molecule is alternatingly reduced and oxidized, and 3. detecting the current generated over the period $t_1$-$t_2$ by repeated reduction and oxidation of the species/molecule in the at least one electrode. In addition, the present invention provides an electrode array for carrying out this process, comprising at least one measuring position and at least one measuring electrode per measuring position as well as a reference electrode, wherein the electrode array is designed such that the measuring electrode can be switched alternatingly as a cathode and as an anode relative to the reference electrode.

23 Claims, 4 Drawing Sheets

(56) References Cited

U.S. PATENT DOCUMENTS

Figure 1:
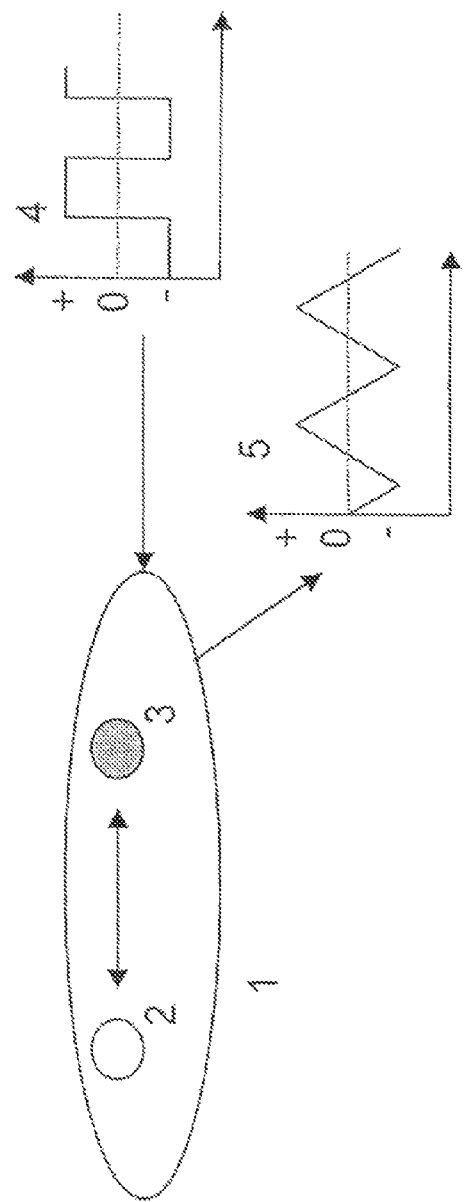

2008/0099347 A1    5/2008   Barlag et al.
2010/0155263 A1*   6/2010   Barlag et al. ............... 205/777.5

FOREIGN PATENT DOCUMENTS

| | | |
|---|---|---|
| DE | 102005007539 A1 | 8/2006 |
| EP | 0886773 B1 | 12/1998 |
| JP | A-H04-118554 | 4/1992 |
| JP | 2001-512691 | 8/2001 |
| JP | 2003-513274 | 4/2003 |
| WO | WO 99/07879 | 2/1999 |
| WO | WO 01/33206 | 5/2001 |
| WO | 02081739 A2 | 10/2002 |
| WO | 02082078 A2 | 10/2002 |
| WO | 2005073708 A2 | 8/2005 |
| WO | 2007014931 A2 | 2/2007 |
| WO | 2007062719 A2 | 6/2007 |

OTHER PUBLICATIONS

Eric Nebling et al., 'Electrical Detection of Viral DNA Using Ultramicroelectrode Arrays': Analytical Chemistry (2004), 76(3); pp. 689-696.

Joerg Albers et al., 'Electrical Biochip Technology—A Tool for Microarrays and Continuous Monitoring', Anal Bioanal. Chem., (2003), 377(3): 521-7.

R. Hintsche et al., 'Fully Electrical Microarrays': Perspectives in Bioanalysis, vol. 1, 2005 Elsevier B.V., pp. 247-277.

Jagotamoy Das et al., 'Electrochemical Immunosensor Using p-Aminophenol Redox Cycling by Hydrazine Combined with a Low Background Current': Analytical Chemistry, vol. 79, No. 7, Apr. 1, 2007, pp. 2790-2796.

Benoit Limoges et al., 'Theory and Practice of Enzyme Bioaffinity Electrodes. Chemical, Enzymatic, and Electrochemical Amplification of in Situ Product Detection'; Journal of the American Chemical Society (2008), 130(23): pp. 7276-7285.

* cited by examiner

METHOD FOR DETECTING CHEMICAL OR BIOLOGICAL SPECIES AND ELECTRODE ARRANGEMENT THEREFOR

The present invention pertains to a process for detecting one or more chemical or biological species, which can either react in a redox reaction or directly or indirectly release a molecule, which can react in a redox reaction, wherein current generated by said redox reaction is detected at at least one electrode position.

Carriers with one or more measuring positions, comprising an electrode, at which only an oxidation or a reduction of a mediator takes place, are state of the art. The preparation of the electrodes for this process is simple (e.g., gold wire, printed circuit boards, metalized plastic), but the current signals obtained often lack sufficient sensitivity.

Ultrafine, interdigital electrode arrays were developed in recent years, where each measuring position has two electrodes with a finger-like structure each and the two finger-like structures mesh with one another such that electrode strips of both electrodes, which said strips are usually parallel, come alternatingly to lie next to each other. The distances between the two electrodes may be markedly less than 1 µm in the favorable case. Such a sensor, in which the structural width of the electrodes is in the sub-µm range, is described, for example, in DE 43 18 519 A1. O. Niwa et al., *Anal. Chem.* (1993), 65, 1559-1563, were able to show that the measured signal was markedly increased compared to detection with the use of a usual, single electrode in case of the cyclovotammetric detection of 4-aminophenol, which was formed by the enzymatic splitting of 4-aminophenyl phosphate by alkaline phosphatase, at electrodes with structural width of 3-5 µm and with a distance of 2-5 µm between the fingers.

EP 886 773 B1 discloses a process for detecting molecules or molecule complexes in a diluent or solvent, wherein a test sample is brought into contact with an interdigital ultramicroelectrode array. By applying an electric potential to the electrode structures, an alternating electric field is generated for the process, and the current or potential changes, which are caused by species present or formed in the test sample, are measured. The resulting current flow is influenced here mainly by the detected molecules and molecule complexes in the space near the electrodes. The influence may take place by diffusion, by addition or by bonding of the species to be measured. The measurements are carried out, in particular, by means of impedance spectroscopy. The electric field used for the detection may be generated by alternating voltage with very small amplitudes between approx. 10 mV and 50 mV; the frequencies may be between 1 mHz and 10 MHz.

The molecules to be measured may be bound to the microelectrode surfaces themselves. This may be brought about by physical bonding (adsorption) or chemical bonding, wherein, e.g., thiol compounds are applied to gold electrodes and measured. However, antigens or the like, which react with an antibody in the test sample, may also be applied to the electrodes, or hybridization reactions can be tracked in nucleic acid chemistry.

The above-mentioned document shows as an exemplary embodiment the detection of the bonding of β-galactosidase-streptavidin to an S-biotinylated electrode surface made of gold. After bonding of the modified streptavidin to the biotin, the change in impedance is measured on the basis of a so-called Nyquist plot, which shows the interference of the dielectric between the electrodes due to the complexed molecule and thus represents the bonding that has taken place between the biotin and the streptavidin-enzyme complex. The ultramicroelectrode array can measure the bonding of β-galactosidase-streptavidin to biotin, in addition, amperometrically on the basis of the detection of p-aminophenol. A constant potential, by which one electrode is brought to a potential of +250 mV relative to an Ag/AgCl reference electrode, by means of which the aminophenol is oxidized into quinoneimine, is superimposed for this to the alternating electric field.

Figure 2A:
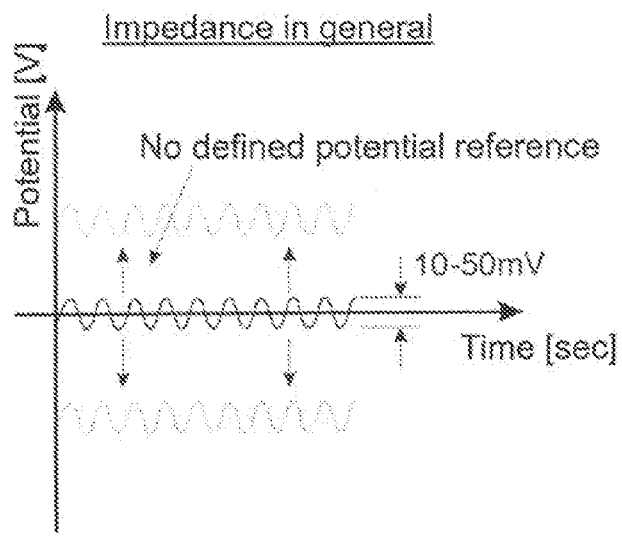

The above-described principle of measurement as well as other possible principles of measurement with the use of interdigital electrodes shall be explained in more detail below:

1. The complex alternating current resistance is measured by pure impedance spectroscopy. This is used in electrochemistry mainly to characterize the medium located between the electrodes and/or special coatings of the electrode surfaces, which are occupied by catcher molecules (e.g., biological catcher molecules bound to gold electrodes via thiol bridges). The presence of a species bonding to the catcher molecules can be found in the detection fluid with a measuring position comprising said interdigital electrodes because the conductivity for electrons and/or protons changes in the environment of the electrodes due to the bonding. If a plurality of measuring positions are provided, these may be possibly coated with different catcher molecules, which bond different species, so that a plurality of species can be detected in one detection fluid. The electrodes themselves are not typically altered chemically by the bonding of the species to be detected to the catcher molecules. The lowest possible a.c. voltage (usually at or below 50 mV), which does not, in general, have to be referred to a reference, is used for this measuring technique. The frequency is varied at times over very broad ranges in order to read further dependences therefrom. A diagram, in which this measurement is plotted on the basis of the coordinates potential [V] over time [sec], is shown in FIG. 2a.

Figure 2B:
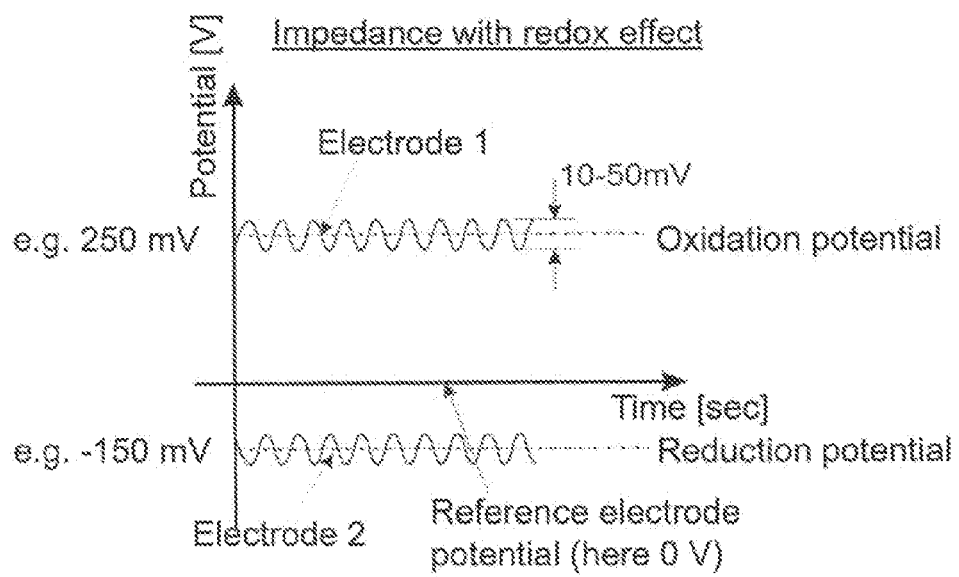

2. Impedance spectroscopy may additionally utilize oxidation and/or reduction effects, as they are mentioned, e.g., in the above document. As in pure impedance spectroscopy, an a.c. resistance is measured by means of a low alternating voltage in the range of usually approx. 10-50 mV. However, using a direct voltage, a defined potential is applied at the same time to at least one of the two electrodes (typically by means of reference to a reference electrode), which said defined potential specifically brings about a reduction or an oxidation of an oxidizable or reducible mediator or of a mediator accessible to a redox reaction, which in turn generates direct currents, which are not, however, necessarily analyzed. What is measured, as a rule, is only the additional effect thereof on the impedance. A corresponding diagram, in which the potential [V] is again plotted against time [sec], is shown in FIG. 2b.

3. Instead of the impedance, cyclic voltammetry may also used as the principle of measurement in these arrays. The electrodes are switched for this very slowly—usually over several seconds or even minutes—from a preset positive voltage to a preset negative voltage and back again. The diagram of the measured strength of electrical current vs. the voltage, which is thus obtained, makes it possible to infer the presence of molecules to be detected between the interdigital electrodes. Cyclovoltammetry is, in principle, a very slow electrochemical redox process with a corresponding conversion of substances, in which oxidation and/or reduction maxima of the corresponding substance are determined.

Figure 2C:
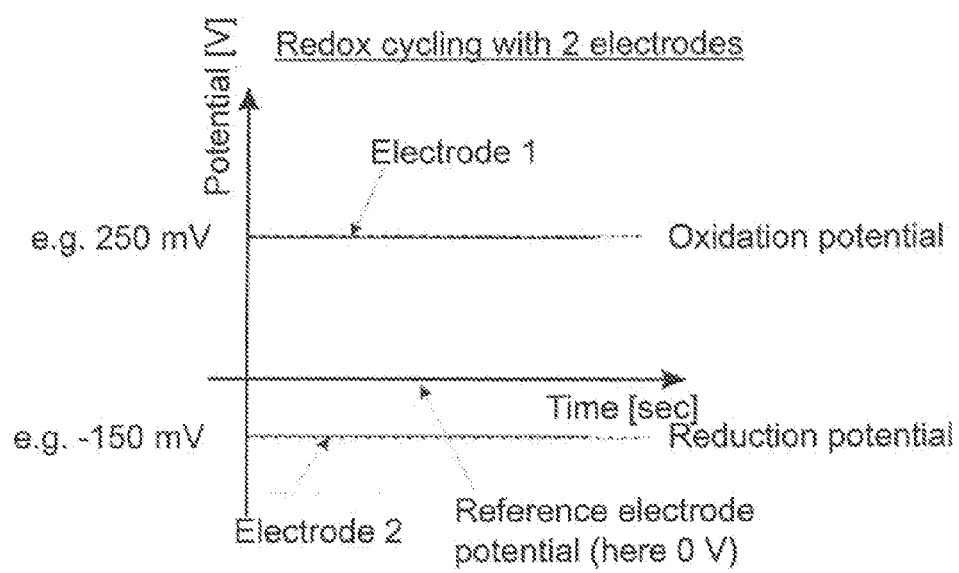

4. Redox cycling, also called redox recycling, differs from these methods. An oxidation potential and a reduction potential (with reference to a reference electrode), which should be at or above the oxidation potential and at or below the reduction potential of the redox molecule to be detected, are constantly applied for this to the two electrodes. Because of the extreme proximity of the two electrodes, the oxidized molecule migrates to the oppositely charged electrode, is reduced there and migrates back again. The two currents, which are generated directly by the oxidation or reduction of the redox molecules at the electrodes, are measured. Every single molecule can be detected multiple times due to the multiple oxidations and reductions, which leads to an amplification of the measured signals. A corresponding diagram, in which the potential [V] is again plotted against time [t], is shown in FIG. 2c.

The drawback of the above-mentioned techniques is that the interdigital electrode structures must be prepared in the sub-μm range in order to make it possible to bring the respective, differently charged electrodes very close to one another. However, this is the only way of carrying out measurements with sufficient sensitivity. This happens currently by means of the complicated semiconductor technology in clean rooms, cf., e.g., E. Nebling et al., *Anal. Chem.* (2004), 76(3), 689-696. Another drawback is that the great proximity of the electrodes to one another implies the risk of short-circuits: Should the anode and cathode touch each other at a distance that is often only about 400 nm, the measuring position in question is unsuitable for use as a whole. Should a plurality of species in a liquid be detected with an electrode array, and should a plurality of measuring positions, coated with different catcher molecules, be exposed to the same liquid to be analyzed, the entire test must be repeated with a new electrode array.

To rule out short-circuits, the electrode structures are often embedded in the substrate. However, this is, of course, associated with a further increase in the manufacturing costs.

The object of the present invention is therefore to remedy this situation and to make it possible to measure molecules or other species, such as molecule complexes, peptides, proteins (especially enzymes), antigens, nucleic acids or species containing nucleic acids, etc., by means of a technique that is more reliable and less demanding concerning the devices to be used.

The object is accomplished by providing a process for detecting one or more (chemical or biological) species, which can either react in a redox reaction or directly or indirectly release a molecule that can react in a redox reaction, wherein current generated by said redox reaction is detected at at least one electrode position, wherein the at least one electrode position, at which or in the proximity of which the species to be detected is located, is switched back and forth multiple times between two different potentials such that relative to a reference electrode, it assumes potentials that are close to or below/above the redox potential of said species or of said molecule, so that said species/said molecule (the latter after having been released) is alternatingly reduced and oxidized at or in the proximity of said electrode position during the switching back and forth. The current generated over time by the repeated reduction and oxidation of the species/molecule is detected and optionally compared with an electrode position at which or in the proximity of which said species or said molecule is not present. The detection and analysis of the strengths of electrical current and the conclusion that the species being sought, which can be qualitatively or quantitatively determined, is present or not, take place, as a rule, according to the features of claim 1, preferably according to claim 2 and optionally also according to claim 3. The term "positioning of a quantity of species variable over time" shall be defined here such that the quantity of the species on, at or in the proximity of the electrodes changes and preferably increases during the period $t_1$-$t_2$.

The process according to the present invention differs from the usual redox cycling in that no interdigital electrodes with a permanently set potential difference need to be used, but the voltage is varied cyclically at only one electrode such that this alternatingly acts as a cathode and anode relative to a reference electrode. This is shown schematically in FIG. 2d. Due to the switching back and forth between two different potentials on said electrode, which switching takes place, as a rule, at a relatively low frequency at, e.g., 0.1 to 10 Hz, a species or molecule that is accessible to a redox reaction is then oxidized by one potential and reduced by the other potential if said species or said molecule is present on or in the proximity of said electrode. The currents generated in the process—a positive oxidation current and a negative reduction current—are measured in their sum (see FIG. 1, in which 1 schematically designates a measuring position comprising an electrode, 2 the oxidized redox mediator, 3 the reduced redox mediator, 4 a low-frequency alternating voltage applied to the electrode and 5 the reading of the generated redox current over time).

What is analyzed here is mainly the change over time in the added-up total current signal (sum of the amounts of oxidation current and reduction current, resulting in an increase in current over time), which corresponds to a change in the concentration of the redox mediator. The capacitive recharging current occurring is not taken into account, because it is independent from the redox currents of the mediator. Even though it relaxes rapidly after each recharging, it is nearly identical in each new measurement cycle and does not consequently change over time.

The sensitivity of this array corresponds approximately to that of the "conventional" redox cycling on an interdigital anode and cathode. However, the complicated manufacturing process for interdigital electrode arrays due to, e.g., the semiconductor technology is eliminated. One or more electrodes with cyclically alternating potentials may be used as a measuring position or as a complete array with different measuring positions.

On the one hand, molecules, which are present in a detection fluid, can be (directly) detected with the process according to the present invention if these molecules can react in a redox reaction. On the other hand, it is possible to detect species that can be bound to the electrodes or to the environment thereof directly or via catcher molecules and directly or indirectly release after their bonding molecules that can in turn react in redox reactions.

The process according to the present invention can be correspondingly used for detecting molecules that are present in a measuring liquid or another detection fluid and are accessible to a redox reaction. Detection fluid shall be defined as liquids, gels or other materials of higher viscosity as well as gases. It is favorable if the detection fluid is guided in a fluid channel over one or more measuring electrodes. A plurality of detection fluids may be able to be measured simultaneously, in which case each of the fluid channels is led over one of the measuring electrodes. It may be favorable now to lead a comparison fluid, which is known to contain or be free from a molecule that is accessible to a redox reaction, over one of the measuring electrodes. This makes it easier to obtain semi-quantitative or quantitative information.

For example, 4-aminophenol can thus be detected directly in a measuring liquid by allowing this liquid to flow into the proximity of measuring electrodes and to stay there for some time. Each electrode is switched continuously at 1.0 Hz back and forth between the redox potentials of p-aminophenol, equaling +200 mV and −350 mV. For example, an iridium/iridium oxide reference electrode may be used as a reference. A counterelectrode, arranged at any point whatsoever, drains off residual currents. A plurality of electrodes, which are located in separate fluid channels each, may be provided in this embodiment as well.

As an alternative, the species to be detected bonds to the electrode structure according to the present invention and/or to the environment thereof directly, for example, by so-called "self-assembling," e.g., via functional groups on said surface and/or functional groups at this species (e.g., proteins bond with SH groups to gold surfaces), or the electrode structure or the immediate environment thereof is coated—via comparable mechanisms—with a catcher molecule, which reacts with the species to be detected and bonds or complexes same, while a product is formed, which converts in turn an added substrate into a molecule that is accessible to a redox reaction (also called redox mediator), whereas the catcher molecule cannot convert the same substrate in the absence of the species to be detected. The redox mediator may be generated here chemically, physically or enzymatically. For example, gold electrodes may be provided, on which a protein is bound by adsorption. One example: Acid phosphatase splits 4-aminophenyl phosphate into the redox molecule 4-aminophenol, and β-galactosidase splits p-aminophenyl-β-galactopyranoside into the same molecule. Any redox molecules may, of course, be used for the present invention; however, those that can be split by enzymes are especially suitable for the detection of enzymes or enzyme-containing complexes. Other examples of suitable redox molecules are ferrocene derivatives, potassium hexacyanoferrate(II), (III) and organic ruthenium and osmium complexes such as ruthenium hexamine, osmium bispyridyl dichloride. However, it is also possible to use other organic and possibly even inorganic redox molecules; the latter are preferably in the encapsulated form, and said capsules may carry, e.g., liposomes, e.g., a group that reacts only with a combination of a catcher molecule and the species to be detected, but not with the catcher molecule alone. Such bonding possibilities are offered, e.g., by so-called intercalation compounds ["sogenannten" in line 36, p. 7 of German original is a typo for "sogenannte"—Tr.Ed.], which are known from DNA technology and react with double-stranded nucleic acid only but not with single-stranded nucleic acid. The person skilled in the art knows a number of possibilities of implementing these techniques, cf., e.g., WO 2002/081739 or WO 2002/082078.

For this process, the detection fluid containing the species is allowed, preferably in a first step, to flow over one or more electrodes, which is/are already coated with the catcher molecules. If a plurality of electrodes are used, the electrodes may be coated with different catcher molecules, which can bond/complex different species. A plurality of different species can therefore be detected in one detection fluid with this process, which is especially significant in DNA analysis. The plurality of electrodes may, of course, be arranged in a common fluid channel or in different fluid channels in this case.

One or more of the electrodes used as measuring positions may remain without catcher molecules in this embodiment. They will then be suitable for use as a comparison electrode to make it possible to compare or calibrate the corresponding measured values with a suitable zero value, which makes it possible to obtain quantitative or semiquantitative detection results.

The electrode/measuring positions may consist of any desired conductive material, e.g., a precious metal such as gold or platinum, but also carbon compounds such as graphite or nanotubes; gold is favorable, because many biologically relevant species can be bound to gold via a thiol bridge. If the measuring positions are coated with biomolecules, they can be used as a platform for a biological test. The redox mediator is generated now, e.g., by an enzyme marking in a position-specific manner or converted into its electrochemically active form.

As was also mentioned above, the immediate environment of the electrode/measuring positions may also be embodied such that it is capable of bonding catcher molecules. For example, materials such as oxides with hydroxide surfaces or modified silanes/siloxanes or inorganic/organic hybrid materials such as the silicon-containing Ormocere® are suitable for this. These can be easily provided or modified on their surface with groups suitable for the present invention, e.g., with amines, hydroxyl groups, and carboxyl groups. Bonding of catcher molecules on the electrode(s) is not usually carried out in the aforementioned cases, but this is not obligatory.

The immediate environment of the electrode/measuring positions may also be made hydrophobic as an alternative or in addition in order to keep the wetting angle of droplets applied to the electrode material (especially for bonding catcher molecules) as great as possible. Instead of this or in addition, the electrode/measuring positions may also be surrounded with rings or webs, which likewise help prevent the running of the droplets of catcher material. Such an embodiment is described, for example, in DE 199 16 867 A1. The rings or webs may be provided permanently or intermediately. The same document also describes punches for applying catcher molecules and for building up microcapillary reactors, embodiments that are equally suitable for the present invention.

The electrode/measuring positions may be arranged on any desired carrier material, for example, on an organic substrate such as plastic, but also on printed circuit boards or the like. A silicon wafer or the like may, of course, also be possibly used as a carrier, even though this will not usually be necessary. The combination of gold electrodes and a plastic substrate is suitable. The electrodes can be applied to the substrate in a simple manner, and so can the conductor structures. The conductor structures may consist of gold or—e.g., to reduce costs—also copper or aluminum or another common material.

The shape of the electrode/measuring positions is not critical, and these may therefore have any desired shape. They may be, for example, flat and have a round, oval, rectangular, elongated stretched, square or other polygonal shape, depending on the requirements imposed on the test and other conditions, such as the arrangement of one or more fluid channels. They may be continuous or have recesses, whose surface is suitable, for example, as described above, for bonding catcher materials. If needed, they may be embedded in the surrounding substrate, for example, in order to improve the flow conditions in the fluid channel, in which they are contained. As an alternative, they may be applied to the substrate, for example, by vapor deposition, printing, plating, soldering or in another manner. These variants are considerably more cost-effective than embedding. The electrode/measuring positions may have any desired size. To make it possible to actuate and measure a plurality of electrodes simultaneously, for example, on a chip, it is, however, favorable to make the area of the electrodes relatively small, e.g., with an area of about 0.05 $mm^2$ to 0.5 $mm^2$. The electrodes may be possibly designed now as microelectrodes or ultramicroelectrodes (with length and/or width dimensions in the μm range or sub-μm range). Finally, it shall be noted that the electrode/measuring positions may possibly also have a three-dimensional structure, e.g., embodied as a drop, solder bump, wire or lamina.

The process typically requires a reference electrode, but this does not have to be located on the same substrate as the measuring electrode(s). It is sufficient for the reference electrode to be located above the detection fluid (e.g., buffer with or without redox species) in conductive connection with the measuring electrodes. No current is admitted to the reference electrode. It consists of a material suitable for the particular process, for example, iridium/iridium oxide, calomel, Ag/AgCl. Furthermore, a counterelectrode, which is charged to a corresponding opposite value to apply the desired current to the measuring electrodes, is needed for the process. This electrode also does not necessarily have to be located on the same substrate as the measuring electrode. It typically, but not necessarily, consists of gold.

The advantage of the process according to the present invention is that an electric reading can be formed on electrodes that may have any desired shape by means of redox cycling, wherein the sensitivity of the reading is comparable to that on interdigital electrode structures. The electrodes can be manufactured in a considerably simpler or more cost-effective manner by avoiding digital structures, because expensive semiconductor and coating techniques with masks, polymer application, exposures and wash-out for the sub-µm electrode structures needed can be eliminated for the conventional redox cycling. In addition, the production yield of these electrodes increases, because rejects due to electric short-circuits, which may be produced in case of the conventional sub-µm interdigital structures, e.g., due to the accidental deposition of particles from the clean room processes, cannot be generated.

The process according to the present invention is preferably used for the so-called chip technology. One measuring position, and preferably a plurality of measuring positions in the form of electrodes is/are located here on a chip, which has, for example, the size of about 50 mm² to 200 mm². A detection fluid or a comparison fluid, e.g., pure buffer, can be admitted to each measuring position. The reference electrode and the counterelectrode may, but do not have to, be likewise arranged on the chip. All electrodes on the chips are connected to electric conductor structures for applying the potentials and for reading the changes in the currents.

The electrical actuation may take place via a separate potentiostat, but it may also be arranged as an electronic component on a separate chip (two-chip solution). This chip is used multiple times, whereas the chip with the measuring positions is used, as a rule, only once and is then discarded, especially if the electrodes or the environment thereof was coated with catcher materials. Finally, it is also possible to arrange the electronic unit directly in the chip, which also carries the measuring positions. All these variants are known from the state of the art, cf., e.g., E. Nebling et al., Electrical Detection of Viral DNA Using Ultramicroelectrode Arrays, *Anal. Chem.* (2004), 76(3): 689-696; J. Albers et al., Electrical Biochip Technology—A Tool for Microarrays and Continuous Monitoring, *Anal. Bioanal. Chem.* (2003), 377(3): 521-527 or R. Hintsche et al., Fully Electrical Microarrays, Electrochemistry of *Nucleic Acids and Proteins*, Toward Electrochemical Sensors for Genomics and Proteomics, 247-277, E. Palecek, F. Scheller and J. Wang (eds.), Elsevier, Amsterdam, 2005.

The present invention shall be explained in more detail below on the basis of exemplary embodiments.

Example 1

A plurality of gold electrodes (diameter 0.5 mm), a counterelectrode and an iridium/iridium oxide reference electrode are applied by vapor deposition on a carrier material, for example, passivated silicon. Each gold electrode corresponds to a measuring position here. An unspecific protein (BSA) is bound by adsorption to the electrodes 1-8. The enzyme β-galactosidase is bound by absorption to the electrodes 9-12. The gold electrodes can be rinsed with various liquid media by means of a microfluidic flow cell, connected to a micropump, tubes and a distributor valve.

The 12 gold electrodes are supplied with the potentials needed with a 16-channel multipotentiostat and the resulting currents are read in the nanoampere range. This potentiostat comprises two 8-fold multiplexers, which sequentially read the electrodes in a short time after application of the corresponding potentials. Switching is performed continuously back and forth at 1.0 Hz at each electrode between the potentials of +200 mV and −350 mV. The iridium/iridium oxide reference electrode is used as a reference. The counterelectrode drains off residual currents. The redox potentials of the mediator p-aminophenol are within the range of +200 mV to −350 mV.

After the washing step with buffer (PBS, pH: 7.0), an enzyme substrate dissolved in buffer (1.0 mg/mL in PBS, pH: 7.0) is charged over the electrodes. This substrate is p-aminophenyl-β-D-galactopyranoside (pAP-β-gal) and is converted by the enzyme β-galactosidase from an electrochemically inactive form into the electrochemically active redox mediator p-aminophenol. The liquid flow is stopped during the electrochemical measurement. As a result, a redox current is or is not generated at each gold electrode independently from the others depending on the presence or absence of the enzyme. This current rises continuously over time at the electrodes carrying enzyme because the enzyme is continuously converting the substrate and thus releases the redox mediator. Consequently, no rise in the current over time is expected at electrodes 1-8 (reference electrodes) and a rise in current over time is expected at electrodes 9-12 (measuring electrodes). The novel electrochemical reading used here is shown in FIG. 3.

Figure 3A:
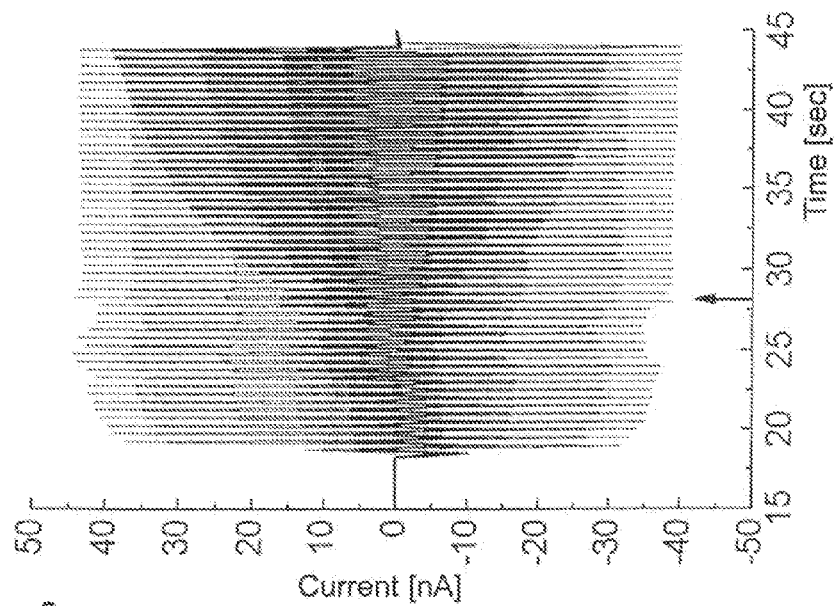

FIG. 3a shows the parallel current measurement over time at every single one of 12 gold electrodes with redox cycling on each electrode on the basis of the resulting measured values of the current signals for all electrodes, which said measured values are one above the other. What is measured is the conversion of p-aminophenol individually at each electrode (+200 mV, −350 mV at 1.0 Hz). After the dissolved substrate has rinsed the gold electrodes completely, the liquid flow is stopped (second 28, see arrow), but the measurement of the current continues. Depending on the potential applied, an oxidation current peak (positive) or a reduction current peak (negative) is obtained. The principal component is the capacitive recharging current, which is, however, averaged out later during the analysis.

Figure 3B:
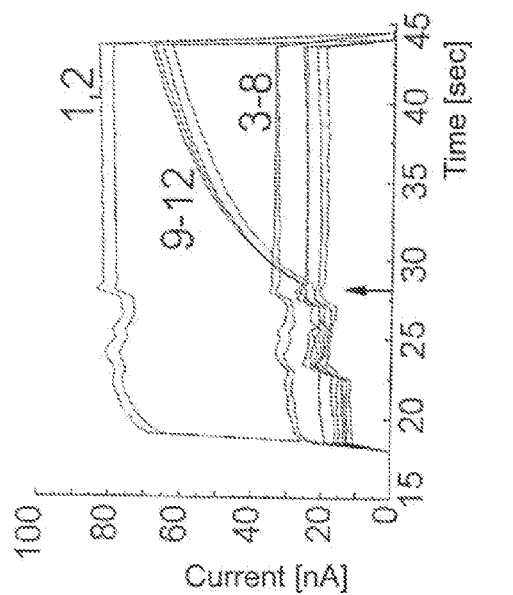

FIG. 3b shows the sum of the current signal quantities from the oxidation current and reduction current for every single electrode (arrow: Stopping of the liquid flow). Positions 1-8 show a largely horizontal curve of the current signals. Positions 9-12 show, by contrast, a rise of the current over time after switching off the liquid flow (arrow). Since the enzyme is absent at electrodes 1-8, no active redox mediator is formed here and no redox currents will consequently result. The enzyme generates the active redox mediator on the electrodes 9-12, and the current rises as a result at these positions continuously over time. Electrodes 1-8 show a different, nearly constant current. This is the capacitive recharging current, which decays rapidly in the msec range after each recharging, but its absolute value per position remains nearly identical during each measurement. The different value of this recharging current from one electrode to the next results from the fact that the potentials are switched over simultaneously at each electrode, but the readings by the multiplexers are slightly offset in time. This recharging current is still high at the electrodes that are measured shortly after the switching (1, 2), because its relaxation has not yet concluded.

Figure 3C:
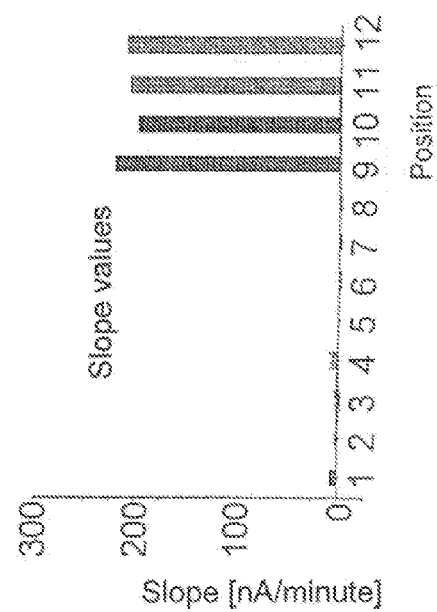

FIG. 3c shows the plotting of the change in the current values over time (rise in current) for each position individually as a bar graph. The currents of the "negative" electrodes 1-8 running horizontally show hardly any change regardless of their value (FIG. 3b). By contrast, the current at the "positive" positions 9-12 rises markedly over time. This unambiguously shows the presence of the enzyme. The mean value of the current rise of positions 9-12 equals about 209 nA/minute.

The redox cycling on interdigital electrodes yields a current rise of about 300 nA/minute in a comparative experimental set-up. If only the oxidation of the mediator is measured at +200 mV, a current rise of about 2 nA/minute is obtained.

The above-described invention is thus suitable for the sensitive electrical reading of redox mediators on non-interdigital electrodes and is considerably more sensitive than only the oxidation on such electrodes, whereas the sensitivity of the reading is comparable to that on interdigital electrodes.

Example 2

To carry out a biological test, the gold electrodes are first coated adsorptively with suitable catcher molecules. A target molecule specifically bound to these catcher molecules is marked by an enzyme (e.g., β-galactosidase). The substrate fed is converted by this enzyme into the active redox mediator. This can be measured sensitively in an electrode-specific manner with the above-described method.

The invention claimed is:

1. Process for detecting one or more chemical or biological species within a liquid, wherein the species either reacts in a redox reaction or directly or indirectly generates a molecule that reacts in a redox reaction, wherein current generated by said redox reaction is detected at the surface of at least one electrode,
comprising the following steps:
positioning a quantity of the species or molecule, which quantity varies over time, on, at or in the proximity of the at least one electrode within a period $t_1$-$t_1'$-$t_2$ by flowing a liquid over the at least one electrode during a time period $t_1$-$t_1'$ and stopping the liquid at the time $t_1'$,
multiple switching of the at least one electrode back and forth during the period $t_1$-$t_1'$-$t_2$ between two different potentials such that relative to a reference electrode, it assumes potentials that are in the range of or above the oxidation potential of said species or of said molecule or are in the range of or below the reduction potential of said species or of said molecule, as a result of which said species/said molecule is alternatingly reduced and oxidized,
detecting the current generated by the repeated reduction and oxidation of the species/molecule in the at least one electrode over the period $t_1$-$t_1'$-$t_2$,
measuring the current flow in the at least one electrode during the time interval $t_1$-$t_1'$-$t_2$,
plotting the current flow during the time interval $t_1$-$t_1'$-$t_2$ over time, and
adding up the absolute values of the current signals, whereby a curve is obtained, which indicates the absolute value of the current flow over time,
characterized in that it is observed for the qualitative detection of the species whether the curve after stopping the liquid is higher in the range $t_1'$-$t_2$ than the curve prior to stopping the liquid in range $t_1$-$t_1'$, or that after stopping the liquid the slope of the current values in range $t_1'$-$t_2$ or the integral under the current values is measured and compared with reference values for a quantitative detection of the species.

2. Process in accordance with claim 1, characterized in that the multiple switching back and forth takes place at a frequency in the range of 0.1 Hz to 10 Hz and/or that the number of switching operations in the time interval $t_1$-$t_2$ is between 10 and 100 and preferably between 15 and 50.

3. Process in accordance with claim 1, wherein one or more species react in a redox reaction, characterized in that the positioning of the specks comprises passing of a fluid containing the species over the at least one electrode.

4. Process in accordance with claim 1, wherein one or more species react in a redox reaction, characterized in that positioning of the species comprises the following steps:
providing catcher molecules on the at least one electrode or in the immediate environment of the electrode, and
passing a fluid containing the species over the at least one electrode and the immediate environment thereof, such that the catcher molecules capture the species by bonding or complexing.

5. Process in accordance with claim 1, wherein one or more species directly or indirectly generate a molecule, which reacts in a redox reaction, characterized in that positioning of the molecule comprises the following steps:
passing a fluid containing the species over the at least one electrode or the immediate environment thereof, such that the species is bound at the at least one electrode or in the immediate environment of the electrode, and
generating the molecule, which reacts in a redox reaction, by the species.

6. Process in accordance with claim 5, characterized in that catcher molecules, which capture the species by bonding or complexing, are arranged on the at least one electrode and/or in the immediate environment thereof.

7. Process in accordance with claim 5, characterized in that to generate the molecule, which reacts in a redox reaction, a fluid, which contains a precursor molecule, from which the species generates said molecule, which reacts in a redox reaction, is passed over the at least one electrode and optionally the immediate vicinity thereof.

8. Process in accordance with claim 5, wherein the species is or contains a protein, especially an enzyme.

9. Process in accordance with claim 8, wherein the enzyme releases p-aminophenol and is preferably selected from among phosphatases and β-galactosidase.

10. Process in accordance with claim 6, wherein the species is a ribonucleic acid, characterized in that the molecule, which reacts in a redox reaction, is generated by the following steps:
passing a fluid, which contains a molecule which binds to the compound or complex of the catcher molecule and the species but not to the catcher molecules alone, and which contains the molecule, which reacts in a redox reaction, in a bound or encapsulated form, over the at least ore electrode and optionally the immediate environment thereof, and
releasing the molecule, which reacts in a redox reaction.

11. Process in accordance with claim 10, wherein the release of the molecule, which reacts in a redox reaction, is brought about by passing another fluid over the at least one electrode and optionally the immediate vicinity thereof, wherein the fluid releases the molecule that reacts in a redox reaction.

12. Process in accordance with claim 1, characterized in that the at least one electrode has a surface consisting of platinum or gold.

13. Process in accordance with claim 1, characterized in that catcher molecules, which bind or complex the species to be detected, are present on the surface of the at least one electrode, wherein the catcher molecules are preferably bound to the electrode via thiol bridges.

14. Process in accordance with claim 1, characterized in that a nonconductive substrate, which is activated such that it binds or adsorbs the species and/or catcher molecules, is located in the immediate vicinity of the at least one electrode.

15. Process in accordance with claim 1, characterized in that at least two electrodes are present, which are switched back and forth in the same direction between said different potentials during the period $t_1$-$t_2$ such that they assume potentials relative to a reference electrode that are in the range of or below/above the redox potential of said species or said molecule, as a result of which said Species/said molecule is alternatingly reduced and oxidized simultaneously at each of the at least two electrodes.

16. Process in accordance with claim 15, characterized in that the two electrodes or two of the electrodes are coated with different catcher molecules, which bond or detect different species.

17. Electrode array for carrying out a process in accordance with claim 1, with at least one measuring position and at least one measuring electrode per measuring position and a reference electrode, which array is designed such that all measuring electrodes are switched alternatingly as a cathode and as an anode in the same direction relative to the reference electrode.

18. Electrode array in accordance with claim 17, comprising a substrate in a chip format and one or more measuring electrodes, which consist of gold or platinum or are coated with gold or platinum.

19. Electrode array in accordance with claim 17, wherein the measuring electrodes have dimensions in the μm range or below the μm range.

20. Device for carrying out a process in accordance with claim 1, comprising an electrode array comprising at least one measuring position and at least one measuring electrode per measuring position and a reference electrode, which array is designed such that all measuring electrodes are switched alternatingly as a cathode and as an anode in the same direction relative to the reference electrode, the device further comprising a counterelectrode as well as a switching device, which switches the measuring electrode(s) alternatingly as a cathode and as an anode in the same direction relative to the reference electrode.

21. Device in accordance with claim 20, characterized in that the switching device is a potentiostat.

22. Device in accordance with claim 20, characterized in that the switching device is an electronic switching device, which is located on or in a substrate, which is not the substrate for the measuring electrode.

23. Device in accordance with claim 20, characterized in that the switching device is an electronic switching device, which is located on or in the same substrate which carries the measuring electrodes.

* * * * *

UNITED STATES PATENT AND TRADEMARK OFFICE
CERTIFICATE OF CORRECTION

| | | |
|---|---|---|
| PATENT NO. | : 8,900,440 B2 | Page 1 of 2 |
| APPLICATION NO. | : 12/995923 | |
| DATED | : December 2, 2014 | |
| INVENTOR(S) | : Nebling et al. | |

It is certified that error appears in the above-identified patent and that said Letters Patent is hereby corrected as shown below:

In the drawings

Figure 2D:
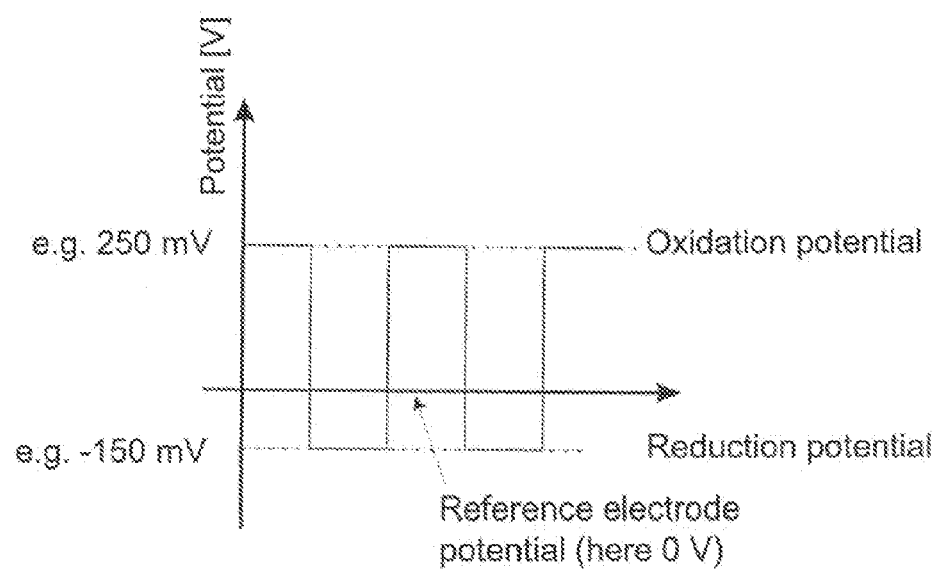

In Figure 2d, Sheet 3 of 4:

--<u>Alternating redox cycling</u>-- should appear above said figure.

In the claims

In Claim 10, Column 10, lines 54-61:

passing a fluid, which contains a molecule which binds to the compound or complex of the catcher molecule and the species but not to the catcher molecules alone, and which contains the molecule, which reacts in a redox reaction, in a bound or encapsulated form, over the at least "ore" electrode and optionally the immediate environment thereof, and releasing the molecule, which reacts in a redox reaction.

should read:

passing a fluid, which contains a molecule which binds to the compound or complex of the catcher molecule and the species but not to the catcher molecules alone, and which contains the molecule, which reacts in a redox reaction, in a bound or encapsulated form, over the at least --one-- electrode and optionally the immediate environment thereof, and releasing the molecule, which reacts in a redox reaction.

Claim 15, Column 11, lines 12-20:

Process in accordance with claim 1, characterized in that at least two electrodes are present, which are switched back and forth in the same direction between said different potentials during the period $t_1$-$t_2$ such that they assume potentials relative to a reference electrode that are in the range of or Signed and Sealed this
Second Day of February, 2016

Michelle K. Lee
*Director of the United States Patent and Trademark Office*

CERTIFICATE OF CORRECTION (continued)
U.S. Pat. No. 8,900,440 B2 below/above the redox potential of said species or said molecule, as a result of which "said Species/said molecule" is alternatingly reduced and oxidized simultaneously at each of the at least two electrodes.

should read:

Process in accordance with claim 1, characterized in that at least two electrodes are present, which are switched back and forth in the same direction between said different potentials during the period $t_1$-$t_2$ such that they assume potentials relative to a reference electrode that are in the range of or below/above the redox potential of said species or said molecule, as a result of which --said species/said molecule-- is alternatingly reduced and oxidized simultaneously at each of the at least two electrodes.